(12) United States Patent
Dohi

(10) Patent No.: US 11,385,211 B2
(45) Date of Patent: Jul. 12, 2022

(54) DETECTOR

(71) Applicant: HOCHIKI Corporation, Tokyo (JP)

(72) Inventor: Manabu Dohi, Tokyo (JP)

(73) Assignee: HOCHIKI CORPORATION, Tokyo (JP)

( * ) Notice: Subject to any disclaimer, the term of this patent is extended or adjusted under 35 U.S.C. 154(b) by 588 days.

(21) Appl. No.: 16/376,866

(22) Filed: Apr. 5, 2019

(65) Prior Publication Data

US 2020/0319154 A1  Oct. 8, 2020

(51) Int. Cl.
  *G01N 33/00*  (2006.01)
  *G08B 17/107*  (2006.01)
  *G01N 21/53*  (2006.01)

(52) U.S. Cl.
  CPC ......... *G01N 33/0016* (2013.01); *G01N 21/53* (2013.01); *G08B 17/107* (2013.01)

(58) Field of Classification Search
  CPC .. G01N 33/0016; G01N 21/53; G01N 21/534; G08B 17/107; G08B 17/10; G08B 17/13
  See application file for complete search history.

(56) References Cited

U.S. PATENT DOCUMENTS

| | | | | |
|---|---|---|---|---|
| 3,708,675 A | * | 1/1973 | Tashiro | G08B 17/107 340/630 |
| 4,914,425 A | * | 4/1990 | Kaminaka | G08B 17/113 340/693.6 |
| 6,521,907 B1 | * | 2/2003 | Shoaff | G08B 17/107 356/628 |
| 2002/0084907 A1 | * | 7/2002 | Rattman | G08B 17/113 340/630 |
| 2020/0160688 A1 | * | 5/2020 | Shimadzu | G01N 21/01 |
| 2021/0088442 A1 | * | 3/2021 | Dohi | G01N 21/53 |

FOREIGN PATENT DOCUMENTS

| | | | |
|---|---|---|---|
| CN | 112614299 A | * | 4/2021 |
| JP | 2011248547 A | | 12/2011 |

* cited by examiner

*Primary Examiner* — Francis C Gray
(74) *Attorney, Agent, or Firm* — Blank Rome LLP

(57) ABSTRACT

To provide a detector capable of reliably inducing a gas containing a detection target to a detection space. A detector which is attached to an installation surface of an installation target and has an attachment surface facing the installation surface includes a detection space into which a detection target flows; a light-emitting portion and a light-receiving portion which detect the detection target flowing into the detection space; a casing which accommodates the light-emitting portion, the light-receiving portion and the detection space; and a rib, an inclined surface, a light shielding portion, a casing side inflow opening, a substrate side outflow opening, a casing side outflow opening, a back plate, and the like which induce gas outside the casing, which is gas containing the detection target, to flow into the detection space inside the casing from an opposite side of the attachment surface of the casing and to flow out from the side of the attachment surface of the casing in a direction substantially orthogonal to the attachment surface.

10 Claims, 6 Drawing Sheets

DETECTOR

FIELD OF THE INVENTION

The present Invention relates to a detector.

DESCRIPTION OF THE RELATED ART

In related art, a fire detector including a chamber into which smoke flows, and a labyrinth provided around the chamber to shield the chamber has been known (for example, refer to JP-A-2011-248547). The fire detector is installed, for example, on a ceiling, and is configured so that an inflow and an outflow of the smoke-containing gas are performed via the labyrinth with respect to the chamber at a position where a distance from the ceiling in a direction substantially orthogonal to the ceiling (hereinafter simply referred to as a "distance from the ceiling") is constant. Further, the fire detector determines a fire by detecting the density of smoke in the gas flowing into the chamber.

Incidentally, in general, since the gas moving toward the detector along the ceiling at the time of fire occurrence is influenced by a friction with the ceiling, the flow velocity is different depending on the distances from the ceiling. Specifically, the flow velocity becomes faster as the distance from the ceiling increases.

However, in the fire detector of the related art, since the inflow and the outflow of the gas are performed at a position where the distance from the ceiling is constant, a pressure difference or a temperature difference due to the difference in the flow velocity of the gas around the chamber (specifically, the inflow side and the outflow side of the gas) does not occur, in other words, it is difficult to induce the gas to the chamber by utilizing the pressure difference or the temperature difference. Further, in the fire detector of the related art, since the labyrinth is provided around the chamber, there is a possibility that the inflow of the gas into the chamber is hindered by the labyrinth. Therefore, in the fire detector of the related art, even if the inflow of smoke into the chamber is hindered by the labyrinth, it is not possible to induce smoke by utilizing the aforementioned pressure difference or temperature difference, and there is a possibility of difficulty in quickly determining the fire. In particular, there is a possibility that it is particularly difficult to quickly determine smoke-burning fire, which often occurs in the early stages of fire, and in which the flow velocity of entire smoke generated is relatively slow.

SUMMARY OF THE INVENTION

It is an object of the present invention to solve the problems of the above-mentioned prior arts.

In order to solve the above-mentioned problem and achieve the purpose, one aspect of the present invention provides a detector which is attached to an installation surface of an installation target and has an attachment surface facing the installation surface, comprising: a detection space into which a detection target flows; a detection unit which detects the detection target flowing into the detection space; an accommodation unit which accommodates the detection unit and the detection space; and an induction unit which induces gas outside the accommodation unit, which is gas containing the detection target, to flow into the detection space inside the accommodation unit from an opposite side of the attachment surface of the accommodation unit and to flow out from the side of the attachment surface of the accommodation unit in a direction substantially orthogonal to the attachment surface.

DETAILED DESCRIPTION OF THE INVENTION

Figure 1:
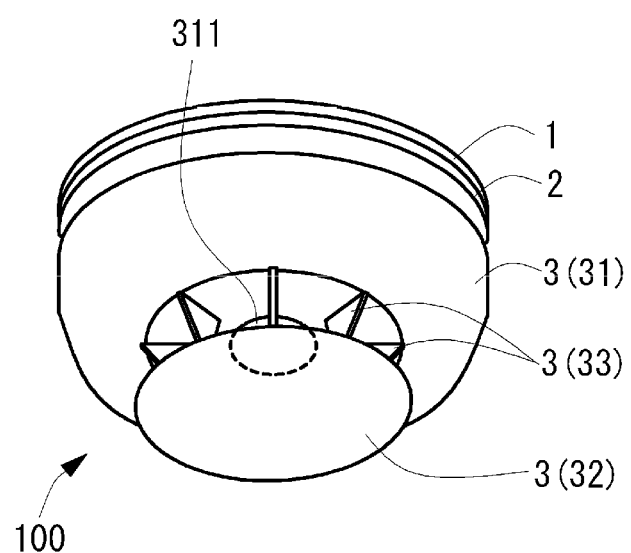
FIG. 1 is a perspective view of a detector according to this embodiment.

Hereinafter, embodiments of a detector according to the invention will be described in detail with reference to the drawings. It should be noted that the invention is not limited by the embodiments.

Basic Concept of Embodiment

First, the basic concept of the embodiment will be described. The embodiment relates generally to a detector including a detection space, a detection unit, an accommodation unit, and an induction unit.

Here, the "detector" is a device which determines an abnormality of a monitoring region, specifically, a device attached to an installation surface of an installation target, and is a device having an attachment surface facing the installation surface, for example, a device that determines an abnormality such as a fire and a gas leak, by detecting the detection target of the monitoring region. The "detector" is a concept including, for example, a smoke detector, a heat detector, a fire detector, a gas leak detector, and the like. Also, the "monitoring region" is a region which becomes a monitoring target of the detector, specifically, a space having a certain spread, an indoor or outdoor space, and is a concept including, for example, a space such as a corridor, a staircase, or a room of a building. Further, the "installation surface" is a surface of an installation target on which the detector is installed, and includes, for example, a surface on the monitoring region side of the ceiling (that is, a lower surface of the ceiling), a surface on the monitoring region side of the wall (that is, an indoor side surface of the wall) and the like. Further, the "attachment surface" is a surface provided on the detector, specifically, a surface which is attached to the installation surface in a state of facing the installation surface. In addition, the "detection target" is a target of detection by the detector, specifically, it relates to an abnormality of the monitoring region, and is a concept including, for example, a toxic gas such as smoke, heat, flame, and carbon monoxide.

In addition, the "detection space" is a space into which a detection target flows, and is, for example, a space in which light is shielded from the outside of the detector in a smoke detector or a fire detector. Further, the "detection unit" is a unit which detects a detection target flowing into the detection space, for example, a unit including a light-emitting unit and a light-receiving unit. The "light-emitting unit" is a unit which emits detection light, and is a concept including, for example, a light-emitting diode or the like. The "light-receiving unit" is a unit which receives light based on the detection light emitted from the light-emitting unit, and is a concept including, for example, a photodiode or the like.

The expression "light based on the detection light emitted from the light-emitting unit" is a concept including a scattered light, which is light generated by scattering of the detection light emitted from the light-emitting unit by a detection target flowing into the detection space, a reflected light generated by reflecting of the detection light emitted from the light-emitting unit within the detection space, extinction light, which is light generated by at least a part of the detection light emitted from the light-emitting unit being blocked and reduced by the detection target, or the like.

Further, the "accommodation unit" at least accommodates the detection unit and the detection space, and constitutes, for example, an outer shape of the detector.

Further, the "induction unit" is a unit which induces a gas so that a gas outside the accommodation unit, which is a gas containing the detection target, flows into the detection space inside the accommodation unit from an opposite side of the attachment surface of the accommodation unit and flows out from the side of the attachment surface of the accommodation unit in a direction substantially orthogonal to the attachment surface. The induction unit is a concept including, for example, a flow path of the gas provided in the accommodation unit, a component for forming the flow path, or the like. The expression "substantially orthogonal" is a concept that includes an intersection at a right angle, an intersection at an angle close to a right angle (for example, 70 to 110 degrees), or the like.

In the embodiment described below, a case where the "detector" is a "fire detector", the "monitoring region" is a "room of a building", and the "detection target" is the "smoke (specifically, smoke particles)" will be described.

(Configuration)

Figure 2:
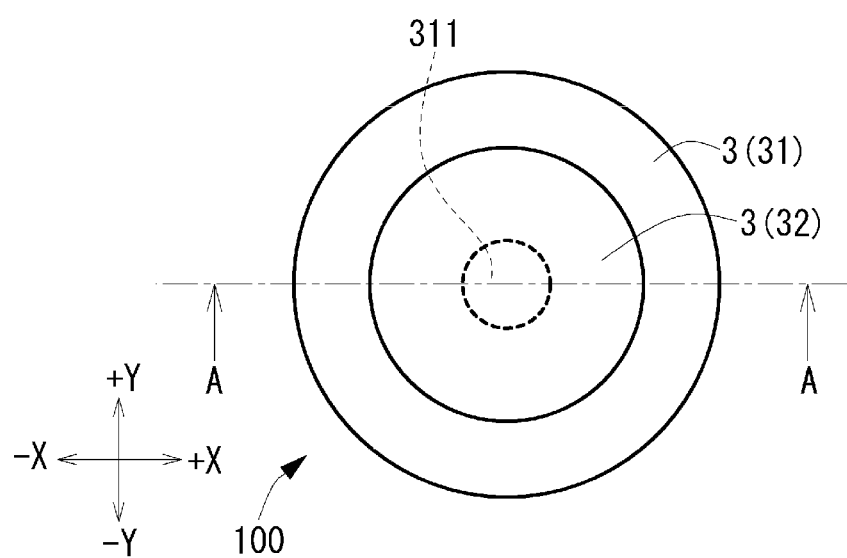
FIG. 2 is a bottom view of the detector.
Figure 3:
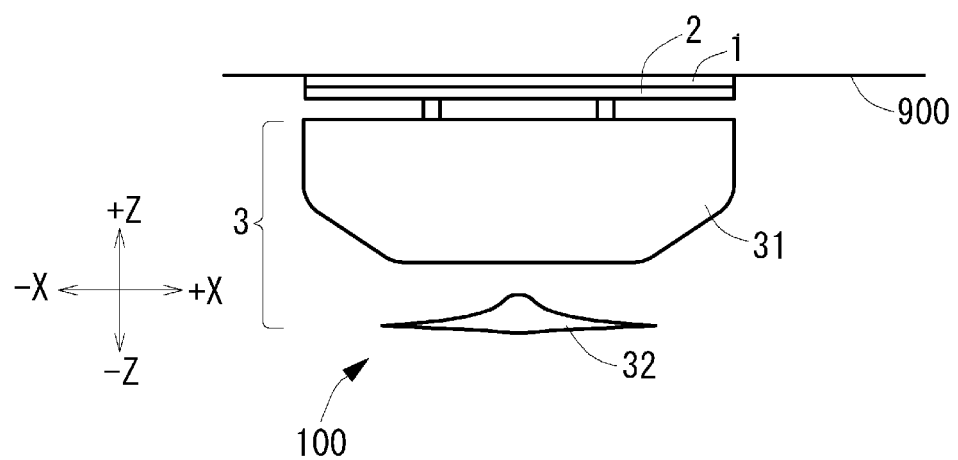
FIG. 3 is a side view of the detector.
Figure 4:
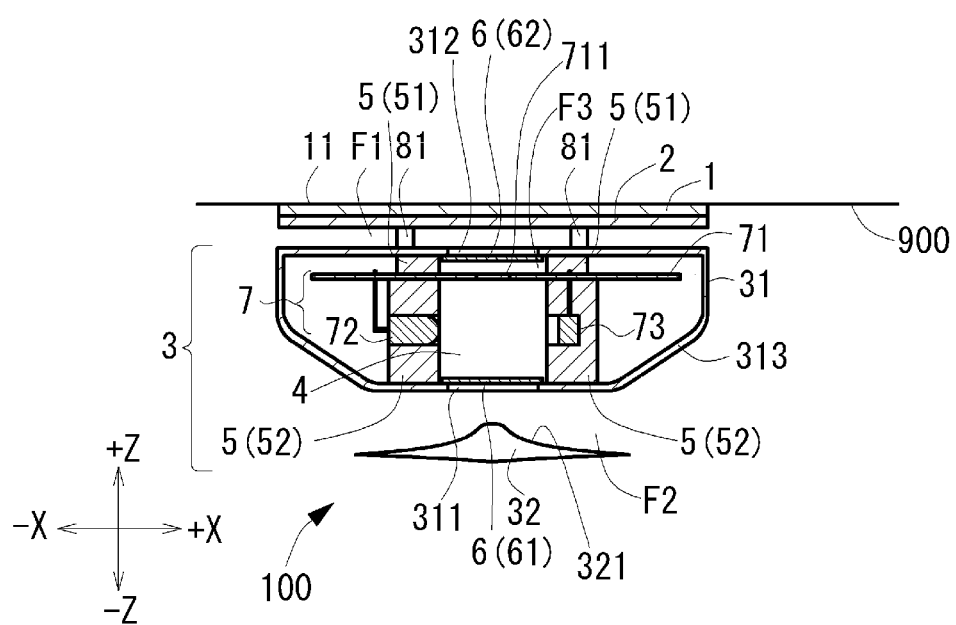
FIG. 4 is a cross-sectional view taken along the line A-A of FIG. 2.

First, the configuration of the detector according to the present embodiment will be described. FIG. 1 is a perspective view of a detector according to the present embodiment, FIG. 2 is a bottom view of the detector, FIG. 3 is a side view of the detector, and FIG. 4 is a cross-sectional view taken along the line A-A of FIG. 2. Further, for convenience of description, a rib 33 of FIG. 1 is omitted in FIGS. 3 and 4, and a power supply line for being supplied with power from a disaster prevention receiver (not illustrated), and a communication line for transmitting a fire signal which is a signal for reporting the fire to the disaster prevention receiver are omitted. In addition, in the following description, X-Y-Z directions illustrated in FIGS. 2 to 4 are directions orthogonal to each other. Specifically, a Z direction is a vertical direction, and an X direction and a Y direction are horizontal directions orthogonal to the vertical direction. For example, the Z direction is referred to as a height direction or a direction substantially orthogonal to an attachment surface 11, a +Z direction is referred to as an upper side (a plane or the attachment surface 11 side in the casing 3), and a −Z direction is referred to as a lower side (a bottom side or an opposite side of the attachment surface 11 in the casing 3). Further, the terms related to the "X-Y-Z directions" below are convenient expressions for describing the relative positional relation (or direction) and the like of each component in an illustrated detector 100. On the basis of a center position of a detection space 4 of FIG. 4, a direction away from the detection space 4 along an XY plane is referred to as "an outer side or an end side", and a direction approaching the detection space 4 is referred to as "an inner side or a center side".

A detector 100 illustrated in each of these drawings is a device which determines a fire by detecting smoke in a monitoring region. Specifically, as illustrated in FIG. 4, the detector 100 is used by being attached to an installation surface 900 which is a ceiling of the monitoring region, and includes, for example, an attachment base 1, a back plate 2, a casing 3, a detection space 4, a support portion 5, an insect repellent net 6, and a circuit portion 7.

(Configuration-Attachment Base)

The attachment base 1 is an attachment unit for attaching the back plate 2 and the casing 3 to the installation surface 900. Although the specific type and configuration of the attachment base 1 are arbitrary, for example, the attachment base 1 includes the attachment surface 11 which is a surface facing the installation surface 900, and is fixed to the back plate 2 and the installation surface 900 between the back plate 2 and the installation surface 900, by a known fixing unit (for example, a screw, a fitting structure, or the like).

(Configuration-Back Plate)

The back plate 2 is an induction unit which induces a smoke-containing gas (hereinafter, simply referred to as a "gas"), and forms, for example, an external outflow side flow path F1 between the back plate 2 and the casing 3. Here, the "external outflow side flow path" F1 is an induction unit which induces the gas, specifically, a flow path for causing the gas in the detection space 4 to flow out to the outside of the detector 100. Although the specific type and configuration of the back plate 2 are arbitrary, the back plate 2 has, for example, a disc shape having the same diameter as that of the casing 3, is fixed to the casing 3 with a spacer 81 interposed therebetween by a known fixing unit (for example, a screw, an adhesive, or the like), and is fixed to the attachment base 1 by a known fixing unit (for example, a screw, a fitting structure, or the like).

(Configuration-Casing)

The casing 3 is an accommodation unit which accommodates the detection space 4, the support portion 5, the insect repellent net 6, and the circuit portion 7 (hereinafter, "the detection space 4, the support portion 5, the insect repellent net 6, and the circuit portion 7" will also be referred to as "accommodation targets"). Although the specific type and configuration of the casing 3 are arbitrary, for example, the casing 3 may include a main body portion 31, a light shielding portion 32, and the rib 33 of FIG. 1.

(Configuration-Casing-Main Body Portion)

The main body portion 31 of FIG. 4 accommodates the accommodation target, and is formed by, for example, a cylindrical portion having the same diameter as the back plate 2 which is a cylindrical portion provided on the upper side (+Z direction) in the height direction (Z direction), and a tapered portion having a diameter to be smaller from the cylindrical portion toward the lower side (−Z direction). Further, the main body portion 31 includes a casing side inflow opening 311, a casing side outflow opening 312, and an inclined surface 313. The casing side inflow opening 311 is an induction unit which induces the gas, specifically, is intended to cause the gas outside the detector 100 to flow into the detection space 4. For example, the casing side inflow opening 311 is provided at the center in a direction parallel to the XY plane, on a surface on the lower side (−Z direction) of the main body portion 31. The casing side outflow opening 312 is an induction unit which induces the gas in the detection space 4, and is intended to cause the gas in the detection space 4 to flow out to the outside of the detector 100. For example, the casing side outflow opening 312 is provided at the center in the direction parallel to the XY plane, on a surface of the upper side (+Z direction) of the main body portion 31. The inclined surface 313 is an induction unit which induces the gas, specifically, is intended to cause the gas outside the detector 100 to flow into the detection space 4, and is provided, for example, in a tapered portion of the main body portion 31.
(Configuration-Casing-Light Shielding Portion)

The light shielding portion 32 is a light shielding unit which shields light from the outer side of the detection space 4, and is an induction unit which induces the gas. As the induction unit, for example, an inflow side flow path F2 is formed between the light shielding portion 32 and the main body portion 31. Here, the "inflow side flow path" F2 is an induction unit which induces the gas, specifically, a flow path for causing the gas outside the detector 100 to flow into the detection space 4. The light shielding portion 32 has, for example, a disc shape having a diameter smaller than the cylindrical portion of the main body portion 31 and slightly larger than the end portion of the lower side (−Z direction) of the tapered portion of the main body portion 31, is fixed to the main body portion 31 via the rib 33 of FIG. 1, and has a facing surface 321 of FIG. 4. Here, the "facing surface" 321 is an induction unit which induces the gas, specifically, is intended to cause the gas outside the detector 100 to flow into the detection space 4, and rises, for example, toward the upper side (+Z direction) from the end side to the center side of the light shielding portion 32 in the direction parallel to the XY plane. Since the light shielding portion 32 having the facing surface 321 is provided in this way, the conventional labyrinth (not illustrated) can be omitted in the detector 100, and the inflow characteristics of the gas into the detection space 4 can be improved.
(Configuration-Casing-Rib)

The rib 33 of FIG. 1 is a reinforcing unit which reinforces the strength of the entire casing 3, and is an induction unit which induces the gas. Specifically, as the induction unit, the rib 33 is intended to cause the gas outside the detector 100 to flow into the detection space 4. The rib 33 has a flat plate shape radially provided on the basis of the casing side inflow opening 311, and a plurality of ribs 33 is provided.
(Configuration-Detection Space)

The detection space 4 of FIG. 4 is a space into which the gas flows. Although the specific type and configuration of the detection space 4 are arbitrary, the detection space 4 is a space provided, for example, at the substantially center side of the casing 3 in a direction along the attachment surface 11 (a direction parallel to the XY plane), and is a space surrounded by a part of the casing 3, an element support portion 52 to be described later, and a circuit board 71 to be described later. Further, the expression "substantially center side of the casing 3 in the direction along the attachment surface 11 (the direction parallel to the XY plane)" is a concept corresponding to a position inside the casing 3, specifically, a position within a predetermined radius (for example, one sixth to one eighth of the width of the casing 3 in the direction along the attachment surface 11 or the like) in the direction along the attachment surface 11, on the basis of the center of the casing 3 in the direction along the attachment surface 11.
(Configuration-Support Portion)

The support portion 5 is a support unit which supports the circuit portion 7. Although the specific type and configuration of the support portion 5 are arbitrary, for example, the support portion 5 includes a substrate support portion 51 and an element support portion 52.
(Configuration-Support Portion-Substrate Support Portion)

The substrate support portion 51 is a support unit which supports the circuit board 71, which will be described later, with respect to the casing 3, and is an induction unit for inducing the gas. Specifically, an internal outflow side flow path F3 is formed as the induction unit. Here, the "internal outflow side flow path" F3 is an induction unit which induces the gas, specifically, a flow path for causing the gas in the detection space 4 to flow out to the outside of the detector 100. The substrate support portion 51 has, for example, a cylindrical shape having an inner diameter larger than a substrate side outflow opening 711 to be described later, and is fixed to the surface on the upper side (+Z direction) of the main body portion 31 and the circuit board 71, between the surface on the upper side (+Z direction) of the main body portion 31 and the circuit board 71 to be described later, by a known fixing unit (for example, a screw, an adhesive, or the like).
(Configuration-Support Portion-Element Support Portion)

The element support portion 52 is a support unit which supports a light-emitting portion 72 and a light-receiving portion 73 to be described later with respect to the casing 3, is a partitioning unit for partitioning the detection space 4, and is an induction unit for inducing the gas. For example, the element support portion 52 has a cylindrical shape having an inner diameter larger than those of the casing side inflow opening 311 and the substrate side outflow opening 711 to be described later. The light-emitting portion 72 and the light-receiving portion 73 are mounted to the element support portion 52. The element support portion 52 is fixed to the surface on the lower side (−Z direction) of the main body portion 31 and the circuit board 71, between the surface on the lower side (−Z direction) of the main body portion 31 and the circuit board 71 to be described later, by a known fixing unit (for example, a screw, an adhesive, or the like).
(Configuration-Insect Repellent Net)

The insect repellent net 6 is an insect repellent unit which prevents insects from entering the detection space 4, and is an inflow unit which causes the gas to flow into the detection space 4. Although the specific type and configuration of the insect repellent net 6 are arbitrary, for example, the insect repellent net 6 includes an inflow side insect repellent net 61 and an outflow side insect repellent net 62.
(Configuration-Insect Repellent Net-Inflow Side Insect Repellent Net)

The inflow side insect repellent net 61 permits the gas to flow into the inside of the detection space 4 from the outside via the small holes of the inflow side insect repellent net 61 itself, while preventing insects from entering the detection space 4. The inflow side insect repellent net 61 has, for example, a diameter larger than the casing side inflow opening 311 as a whole, and is provided to cover the casing side inflow opening 311.
(Configuration-Insect Repellent Net-Outflow Side Insect Repellent Net)

The outflow side insect repellent net 62 permits the gas to flow out to the outside from the inside of the detection space 4 via the internal outflow side flow path F3, via the small hole of the outflow side insect repellent net 62 itself, while preventing insects from entering the detection space 4 via the internal outflow side flow path F3. For example, as a whole, the outflow side insect repellent net 62 has a diameter larger than that of the casing side outflow opening 312, and is provided to cover the casing side outflow opening 312.
(Configuration-Circuit Portion)

The circuit portion 7 is a circuit unit which forms an electric circuit for determining the fire by detecting smoke as a detection target. Although the specific type and configuration of the circuit portion 7 are arbitrary, for example, the circuit portion 7 includes the circuit board 71, the light-emitting portion 72, and the light-receiving portion 73.

(Configuration-Circuit Portion-Circuit Board)

The circuit board 71 is a mounting unit on which each element of the detector 100 is mounted. The circuit board 71 spreads, for example, along the XY plane as a whole, and is supported and fixed by the support portion 5. Further, the circuit board 71 is provided with the substrate side outflow opening 711. The substrate side outflow opening 711 is an induction unit which induces the gas. Specifically, the substrate side outflow opening 711 is intended to cause the gas in the detection space 4 to flow out to the outside of the detector 100 via the internal outflow side flow path F3. For example, the substrate side outflow opening 711 has a diameter smaller than the inner diameter of the substrate support portion 51 and the inner diameter of the element support portion 52, and is provided at the center of the circuit board 71 in the direction parallel to the XY plane.

(Configuration-Circuit Portion-Light-Emitting Portion)

The light-emitting portion 72 is a detection unit for detecting the smoke flowing into the detection space 4, specifically, a light-emitting unit which emits detection light, which is light for detecting the smoke, toward the detection space 4. Although the specific type and configuration of the light-emitting portion 72 are arbitrary, for example, the light-emitting portion 72 includes a light-emitting diode or the like.

(Configuration-Circuit Portion-Light-Receiving Portion)

The light-receiving portion 73 is a detection unit for detecting the smoke flowing into the detection space 4, specifically, a light-receiving unit for receiving the scattered light generated in the detection space 4. Although the specific type and configuration of the light-receiving portion 73 are arbitrary, for example, the light-receiving portion 73 includes a photodiode or the like.

(Induction of Gas)

Figure 5:
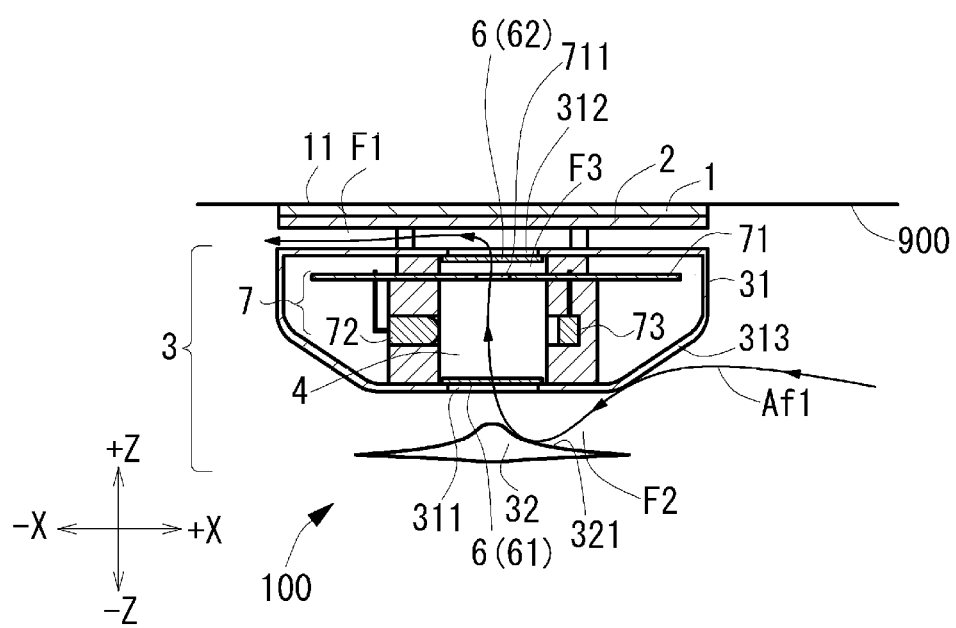
FIG. 5 is a view exemplifying air flow in FIG. 4.

Next, the induction of gas in the detector 100 configured as described above will be described. FIG. 5 is a diagram exemplifying the air flow of FIG. 4. Incidentally, an arrow Af1 of FIG. 5 exemplifies a direction of the air flow based on a result of a predetermined experiment, simulation or the like about the flowing direction of the smoke-containing gas (that is, the direction of the air flow). The detector 100 can induce the gas from all directions outside the casing 3 to flow into the detection space 4 from the lower side (−Z direction) in the height direction (Z direction) and then to flow out from the upper side (+Z direction). Here, for example, the case of inducing the gas along the arrow Af1 of FIG. 5 will be described.

When a fire occurs in the monitoring region, the gas (smoke-containing gas) outside the detector 100 of FIG. 5 moves along the installation surface 900 (alternatively, in parallel to the installation surface 900) toward the detector 100, as illustrated by the arrow Af1, due to the hot air flow based on the fire. Thereafter, the gas is induced to the detection space 4 via the inflow side flow path F2, the casing side inflow opening 311, and the small holes of the inflow side insect repellent net 61. Specifically, the gas is induced from the main body portion 31 side to the light shielding portion 32 side along the inclined surface 313 of the casing 3, and then is induced to the detection space 4 side of FIG. 5 along the facing surface 321 of the light shielding portion 32 and the rib 33 of FIG. 1. In particular, in the gas moving toward the detector 100 along the installation surface 900 (or in parallel to the installation surface 900) at the time of a fire occurrence, in general, the flow velocity becomes faster as going further away from the installation surface 900 to the lower side (−Z direction). For this reason, a temperature difference or a pressure difference occurs due to the difference in the flow velocity, and it is possible to reliably induce the gas to the detection space 4, by moving the gas outside the detector 100 as described above from a side on which the flow velocity is fast, which is the lower side (−Z direction) of the casing 3, to a side on which the flow velocity is slow, which is the upper side (+Z direction) of the casing 3.

Thereafter, as indicated by the arrow Af1, the gas induced to the detection space 4 is induced to the outside of the detector 100, via the substrate side outflow opening 711, the internal outflow side flow path F3, the small holes of the outflow side insect repellent net 62, the casing side outflow opening 312, and the external outflow side flow path F1.

(Determination of Fire)

Next, determination of the fire in the detector 100 configured as described above will be described. A control unit (for example, a CPU or the like) (not illustrated) of the circuit board 71 of the detector 100 determines the fire in the same manner as in a known method. That is, the control unit detects the density of smoke, using the light-emitting portion 72 and the light-receiving portion 73, and then determines the fire on the basis of the detected density of smoke.

Effects of Embodiment

As described above, according to the present embodiment, since the smoke-containing gas is induced to flow into the detection space 4 inside the casing 3 from the opposite side of the attachment surface 11 of the casing 3 in the direction substantially orthogonal to the attachment surface 11, and to flow out from the attachment surface 11 side of the casing 3, for example, a pressure difference or a temperature difference due to the difference in the flow velocity of the gas moving outside the casing 3 occurs between the inflow side and the outflow side of the gas. Accordingly, it is possible to reliably induce the smoke-containing gas to the detection space 4, by utilizing the difference.

Further, since the detection space 4 is provided substantially at the center side of the casing 3 in the direction along the attachment surface 11, for example, it is possible to rapidly and reliably induce the gas, which moves from all directions of the detector 100 in the direction along the attachment surface 11 toward the detector 100, to the detection space 4. Further, for example, since the center of gravity of the detector 100 in the direction along the attachment surface 11 can be configured to be substantially on the center side of the detector 100, the center of gravity is well balanced, and it is possible to provide the detector 100 in which the attaching work or the like is easily performed and the workability is excellent.

Modified Example of Embodiment

Although the embodiments according to the invention have been described above, the specific configuration and unit of the invention can be arbitrarily modified and improved within the scope of the technical idea of each invention described in the claims. Hereinafter, such a modified example will be described.

(Problem to Be Solved and Advantageous Effects of Invention)

First, problems to be solved by the invention and advantageous effects of the invention are not limited to the contents described above, and there is a possibility that they may differ depending on the implementation environment and the details of configuration of the invention, and only some of the above-described problems may be solved, or only a part of the above-described effects may be exhibited.

(Dispersion and Integration)

Further, the above-described configuration is functionally conceptual, and does not necessarily need to be physically configured as illustrated in the drawings. In other words, specific forms of dispersion and integration of each part are not limited to those illustrated in the drawings, and all or a part thereof may be configured by being dispersed or integrated functionally or physically in arbitrary units.

(Detection Space)

Further, in the aforementioned embodiment, a case where the detection space 4 of FIG. 4 is provided substantially on the central side of the casing 3 in the direction along the attachment surface 11 (the direction parallel to the XY plane) has been described, but the embodiment is not limited thereto. For example, the detection space 4 may be provided on the end side of the casing 3 in the direction along the attachment surface 11 (the direction parallel to the XY plane). Here, the expression "the end side of the casing 3 in the direction along the attachment surface 11 (the direction parallel to the XY plane)" is a position inside the casing 3, specifically, a position other than "the substantially center side of the casing 3 in the direction along the attachment surface 11 (the direction parallel to the XY plane)" and is a concept corresponding to the position separated from a predetermined radius (for example, one sixth to one eighth of the width of the casing 3 in the direction along the attachment surface 11 or the like) in the direction along the attachment surface 11, on the basis of the center of the casing 3 in the direction along the attachment surface 11. More specifically, in FIG. 4, the detection space 4 may be provided only on the left side of the drawing, may be provided only on the right side of the drawing, or a total of two detection spaces 4 may be provided on both the left side of the drawing and the right side of the drawing. In this case, positions of elements other than the detection space 4 may be appropriately changed. Further, in FIG. 4, in a case where the detection space 4 is provided only on the left side of the drawing, or in a case where the detection space 4 is provided only on the right side of the drawing, by providing the detection space 4 on the end side of the casing 3 in the direction along the attachment surface 11, for example, it is possible to combine the mounting space of components inside the casing 3 into one place. Thus, it is possible to secure a relatively wide mounting space and to provide a detector 100 having excellent component mountability.

(Back Plate and Attachment Base)

In addition, the attachment base 1 may be omitted after the back plate 2 of FIG. 4 of the above-mentioned embodiment is configured to be directly attached to the installation surface 900. In this case, the surface on the upper side (+Z direction) of the back plate 2 corresponds to the "attachment surface". Further, the attachment base 1 of FIG. 4 of the above-mentioned embodiment is not omitted, the back plate 2 may be omitted, and then the attachment base 1 may be fixed to the casing 3 with a spacer 81 interposed therebetween.

(Internal Configuration of Casing)

Further, after arbitrarily changing the inner diameter of each support portion 5 of FIG. 4 of the aforementioned embodiment, the position or the size of the casing side inflow opening 311, the substrate side outflow opening 711, or the casing side outflow opening 312 may be arbitrarily changed. Specifically, the casing side inflow opening 311, the substrate side outflow opening 711, and the casing side outflow opening 312 may be arranged so as not to be aligned in a line in the height direction (Z direction).

(Air Flow Generation Unit)

Further, the detector 100 of FIG. 4 of the above-mentioned embodiment may be provided with an air flow generation portion (an air flow generation unit) which generates air flow for inducing the gas, for example, along the arrow Af1 of FIG. 5. Specifically, a micro pump using a known piezoelectric element, a known heat generation element that generates heat, a known heat absorption element that absorbs heat, or the like may be provided inside or outside the detection space 4, as the air flow generation portion. Further, a control unit (for example, a CPU or the like) (not illustrated) of the circuit board 71 may control the air flow generation unit on the basis of a predetermined program.

(Attachment of Detector)

Further, in the aforementioned embodiment, a case where the detector 100 of FIG. 4 is attached to the installation surface 900, which is a ceiling of the monitoring region, has been described, but the invention is not limited thereto. For example, the detector 100 may be used by being attached to the wall of the monitoring region.

(Application of Known Configuration)

Further, the detector 100 of FIG. 4 of the aforementioned embodiment may be modified to include the configuration of a known detector. For example, any modification including a modification made for the detector 100 to perform wireless communication with a disaster prevention receiver (not illustrated), a modification to operate the detector 100 by providing a battery in the detector 100 and using the electric power of the battery, or the like may be performed.

(Application to Detector)

In addition, the features of the detector 100 of FIG. 4 of the aforementioned embodiment may be applied to a known scattered light type detector or may be applied to a known light extinction type detector.

(Integral Configuration)

Further, arbitrary components of the detector 100 of FIG. 4 of the above-mentioned embodiment may be configured integrally. For example, the substrate support portion 51, the element support portion 52, and the spacer 81 may be formed integrally.

(Thermal Welding)

Further, arbitrary components of the detector 100 of FIG. 4 of the aforementioned embodiment may be fixed by thermal welding. For example, the element support portion 52 may be thermally welded and fixed between the surface on the lower side (−Z direction) of the main body portion 31 and the circuit board 71.

(Substrate Side Outflow Opening)

Further, the circuit board 71 of FIG. 4 may be provided with a substrate side outflow notch, together with the substrate side outflow opening 711 or instead of the substrate side outflow opening 711. Here, the "substrate side outflow notch" is an induction unit for inducing the gas. Specifically, the substrate side outflow notch is intended to cause the gas in the detection space 4 to flow out to the outside of the detector 100 via the internal outflow side flow path F3. The shape of the substrate side outflow notch is arbitrary, and, although it is not illustrated, for example, the substrate side outflow notch may be formed by notching into a V shape or a U shape from the edge side toward the central side of the circuit board 71 in the direction parallel to the XY plane of FIG. 4.

(Light Shielding Portion)

Figure 6:
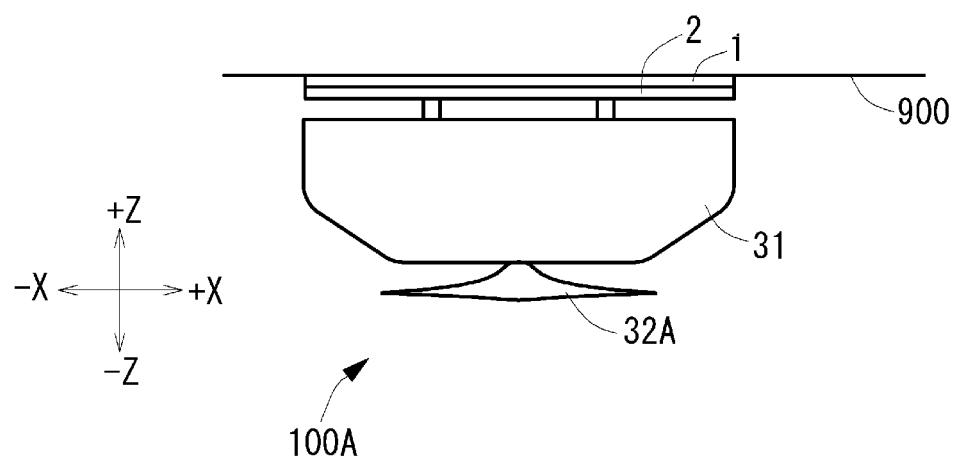
FIG. 6 is a side view of a detector of a modified example.

Further, although a case where the light shielding portion 32 is provided away from the main body portion 31 as illustrated in FIG. 3 has been described in the above-described embodiment, the position of the light shielding portion 32 may be arbitrarily changed. FIG. 6 is a side view of a detector of the modified example. For example, as illustrated in FIG. 6, a light shielding portion 32A of FIG. 6 corresponding to the light shielding portion 32 of FIG. 3 may be provided to be in contact with the side of the main body portion 31 to constitute a detector 100A. Specifically, the light shielding portion 32A may be configured to be in contact with at least a part of the main body portion 31 itself, and the light shielding portion 32A may be configured to be in contact with, for example, the insect repellent net 6 or the like, which is an element on the side of the main body portion 31.

(Features)

Further, the features of the above-mentioned embodiment and the features of the modified example may be arbitrarily combined with each other.

(Notes)

The above embodiments have been made to solve the above-mentioned problems in the conventional technology, and an object of the above embodiments is to provide a detector capable of improving the reliability and mountability.

In order to solve the above-mentioned problem and achieve the above-mentioned purpose, one aspect of a detector of the above mentioned embodiments is a detector which is attached to an installation surface of an installation target and has an attachment surface facing the installation surface, comprising: a detection space into which a detection target flows; a detection unit which detects the detection target flowing into the detection space; an accommodation unit which accommodates the detection unit and the detection space; and an induction unit which induces gas outside the accommodation unit, which is gas containing the detection target, to flow into the detection space inside the accommodation unit from an opposite side of the attachment surface of the accommodation unit and to flow out from the side of the attachment surface of the accommodation unit in a direction substantially orthogonal to the attachment surface.

According to this aspect of the embodiment, since the gas is induced to flow into the detection space inside the accommodation unit from the opposite side of the attachment surface of the accommodation unit in the direction substantially orthogonal to the attachment surface, and to flow out from the attachment surface side of the accommodation unit, for example, a pressure difference or a temperature difference due to the difference in the flow velocity of the gas moving outside the accommodation unit occurs between the inflow side and the outflow side of the gas. Accordingly, it is possible to reliably induce the target-containing gas to the detection space, by utilizing the difference.

Another aspect of the embodiments provides the detector, wherein the detection space is provided substantially at a central side of the accommodation unit in a direction along the attachment surface.

According to this aspect of the embodiment, since the detection space is provided substantially at the center side of the accommodation unit in the direction along the attachment surface, for example, it is possible to rapidly and reliably induce the gas, which moves from all directions of the detector in the direction along the attachment surface toward the detector, to the detection space. Further, for example, since the center of gravity of the detector in the direction along the attachment surface can be configured to be substantially on the center side of the detector, the center of gravity is well balanced, and it is possible to provide the detector in which the attaching work or the like is easily performed and the workability is excellent.

Another aspect of the embodiments provides the detector, wherein the detection space is provided on an end side of the accommodation unit in a direction along the attachment surface.

According to this aspect of the embodiment, by providing the detection space on the end side of the accommodation unit in the direction along the attachment surface, for example, it is possible to combine the mounting space of components inside the accommodation unit into one place. Thus, it is possible to secure a relatively wide mounting space and to provide a detector having excellent component mountability.

REFERENCE SIGNS LIST

1 Attachment base
2 Back plate
3 Casing
4 Detection space
5 Support portion
6 Insect repellent net
7 Circuit portion
11 Attachment surface
31 Main body portion
32 Light shielding portion
32A Light shielding portion
33 Rib
51 Substrate support portion
52 Element support portion
61 Inflow side insect repellent net
62 Outflow side insect repellent net
71 Circuit board
72 Light-emitting portion
73 Light-receiving portion
81 Spacer
100 Detector
100A Detector
311 Casing side inflow opening
312 Casing side outflow opening
313 Inclined surface
321 Facing surface
711 Substrate side outflow opening
900 Installation surface
Af1 Arrow
F1 External outflow side flow path
F2 Inflow side flow path
F3 Internal outflow side flow path

What is claimed is:

1. A detector which is attached to an installation surface of an installation target and has an attachment surface facing the installation surface, comprising:
    a detection space into which a detection target flows;
    a detection unit which detects the detection target flowing into the detection space;
    an accommodation unit which accommodates the detection unit and the detection space; and
    an induction unit which induces gas outside the accommodation unit, which is gas containing the detection target, to flow into the detection space from an opposite side of the attachment surface of the detection space and to flow out of the detection space from the side of the attachment surface of the detection space in a direction substantially orthogonal to the attachment surface, wherein the induction unit comprises a circuit board having a plane along the installation surface and mounting an electric circuit for determining fire by detecting the detection target, the circuit board having a substrate side outflow opening or a substrate side outflow notch that allows the gas flowing from the opposite side of the attachment surface of the detection space to flow toward the side of the attachment surface of the detection space in the direction substantially orthogonal to the attachment surface.

2. The detector according to claim 1, wherein the detection space is provided substantially at a central side of the accommodation unit in a direction along the attachment surface.

3. The detector according to claim 1, wherein the detection space is provided on an end side of the accommodation unit in a direction along the attachment surface.

4. A detector for attachment to an installation surface of an installation target, the detector comprising:
- an attachment surface configured to face the installation surface;
- a detection space into which a detection target flows;
- a detection unit which detects the detection target flowing into the detection space;
- an accommodation unit which accommodates the detection unit and the detection space; and
- an induction unit which induces gas outside the accommodation unit, which is gas containing the detection target, to flow into the detection space at a side thereof that is opposite the attachment surface, in a direction substantially orthogonal to the attachment surface, and to flow out of the detection space from a side thereof that is at the attachment surface, in a direction substantially orthogonal to the attachment surface.

5. The detector of claim 4, wherein the induction unit comprises a circuit board that has an electric circuit for determining fire by detecting the detection target, the circuit board has a substrate side outflow opening configured to allow the gas flowing from the side of the detection space that is opposite of the attachment surface to flow toward the side of the detection space that is at the attachment surface in the direction substantially orthogonal to the attachment surface.

6. The detector of claim 4, wherein the accommodation unit comprises a casing that has an inclined surface configured to induce the gas to flow into the detection space.

7. The detector of claim 6, wherein the casing includes a light shielding portion configured to shield light from the detection space.

8. The detector of claim 7, wherein the light shielding portion includes a raised facing surface configured to induce the gas to flow into the detection space.

9. The detector of claim 4, wherein the detection unit is a light-emitting portion or a light-receiving portion configured to detect the detection target flowing into the detection space.

10. The detector of claim 9, wherein the detection target is smoke.

\* \* \* \* \*